(12) United States Patent
Harrigan et al.

(10) Patent No.: US 10,420,853 B2
(45) Date of Patent: Sep. 24, 2019

(54) FRAGRANCE AND CHEMICAL DISPENSERS AND METHODS FOR USING THE SAME

(71) Applicant: Silgan Dispensing Systems Corporation, Grandview, MO (US)

(72) Inventors: Kelly A. Harrigan, Richmond, VA (US); William T. Riley, Lee's Summit, MO (US); Devin R. Jensen, Henrico, VA (US)

(73) Assignee: Silgan Dispensing Systems Corporation, Grandview, MO (US)

( * ) Notice: Subject to any disclaimer, the term of this patent is extended or adjusted under 35 U.S.C. 154(b) by 42 days.

(21) Appl. No.: 15/166,547

(22) Filed: May 27, 2016

(65) Prior Publication Data

US 2016/0346420 A1    Dec. 1, 2016

Related U.S. Application Data

(60) Provisional application No. 62/167,587, filed on May 28, 2015.

(51) Int. Cl.
| | | |
|---|---|---|
| *A61L 9/12* | (2006.01) | |
| *A01M 29/12* | (2011.01) | |
| *A61L 9/04* | (2006.01) | |
| *A01M 1/20* | (2006.01) | |

(52) U.S. Cl.
CPC .......... *A61L 9/127* (2013.01); *A01M 1/2033* (2013.01); *A01M 1/2044* (2013.01); *A01M 1/2055* (2013.01); *A01M 1/2077* (2013.01); *A01M 29/12* (2013.01); *A61L 9/042* (2013.01); *A61L 9/048* (2013.01); *A01M 2200/01* (2013.01); *A61L 2209/133* (2013.01); *A61L 2209/135* (2013.01)

(58) Field of Classification Search
CPC ...... A61L 9/12; A61L 9/127; A61L 2209/133; A61L 2209/135; A61L 9/042; A61L 9/048; B65D 1/0292; B65D 21/086; A01M 1/2033; A01M 1/2044; A01M 1/2055; A01M 1/2077; A01M 29/12; A01M 2200/01
USPC ....................................... 239/34–60; 220/666
See application file for complete search history.

(56) References Cited

U.S. PATENT DOCUMENTS

| | | | | |
|---|---|---|---|---|
| 3,301,293 A * | 1/1967 | Santelli | ............... | B65D 1/0292 220/666 |
| 4,165,835 A * | 8/1979 | Dearling | .................. | A61L 9/12 239/45 |
| 4,220,281 A * | 9/1980 | Martens, III | ......... | A61B 5/0816 239/57 |
| 4,858,831 A * | 8/1989 | Spector | .................... | A61L 9/12 239/326 |
| 2008/0286143 A1 * | 11/2008 | Grodsky | .................. | A61L 9/12 422/4 |
| 2009/0261114 A1 * | 10/2009 | McGuire | ................. | G09F 23/00 220/666 |
| 2015/0201604 A1 * | 7/2015 | Cao | .................... | A01M 1/2055 239/44 |

(Continued)

*Primary Examiner* — Arthur O. Hall
*Assistant Examiner* — Tuongminh N Pham
(74) *Attorney, Agent, or Firm* — Barlow, Josephs & Holmes, Ltd.

(57) ABSTRACT

Dispensers for fragrance and chemical compounds include paperboard materials and unique shapes to allow for simplified production and use of the dispensers in various environments.

7 Claims, 7 Drawing Sheets

(56) References Cited

U.S. PATENT DOCUMENTS

2015/0251809 A1\* 9/2015 Jasin ................... F41H 3/00
220/8

\* cited by examiner

FRAGRANCE AND CHEMICAL DISPENSERS AND METHODS FOR USING THE SAME

BACKGROUND OF THE INVENTION

Field of the Invention

The present invention relates to the dispensing of fragrances or chemicals and more particularly to dispensers for dispensing fragrances or chemicals into the air.

State of the Art

Air care and air fragrance dispensers are well known. From candles to solid or semi-solid fragrance materials that emanate fragrance into the air in order to provide a scent to an area have been used for years. Similarly, scented oils, scented alcohol, and other liquids have been used to produce or introduce a scent or fragrance within a room. Some dispensers utilize heat or other energy to release fragrances from such oils.

For example, many of the air freshener or air care products available on the market include plug-in systems with a reservoir holding a scented oil or alcohol. Electricity warms the product in the reservoir, releasing a scent. In other examples, scented oils or liquids may wick through a wicking material from a reservoir to an exposed end where evaporation of the product at the wick end releases a scent into the air.

Other devices are also used to release chemicals into the air. For example, devices are used to disperse mosquito or bug repellant into the air around a user. Many such devices exist and take different forms.

While various products exist to facilitate the release of a scent or fragrance or chemical from a product stored in a reservoir into the air, there is a need to develop new dispensers and methods for releasing such scents, fragrances, and chemicals.

BRIEF SUMMARY OF THE INVENTION

According to various embodiments of the invention, a fragrance or chemical dispenser may include a paperboard or plastic body with a hollow interior portion containing a scented product. The scented product may include gels, liquids, solids, or any combination thereof. The body may accordion such that it may be shipped in a smaller form than when in use. According to certain embodiments of the invention, the body is shipped in a compressed format with a product inside. Upon desired use, a user may pull the ends of the body apart, allowing the body to grow or expand as an accordion does. Upon expansion, a product reservoir, hollow area, or other container within an interior of the body may be opened such that a product contained in the product reservoir is exposed to air circulating through the body through holes in the body, natural airflow through the body material, or through controlled flow of air through the body. Air flowing over the product may evaporate the product and release a scent that may be carried to the area around the body, thereby scenting the air in the vicinity of the body.

According to other embodiments of the invention, an accordion body may include a scent or scented particles contained in that portion of the body that pulls apart upon use. When the body is pulled apart, the accordion sidewalls may be exposed to air and the product embedded in the sidewalls may begin to evaporate or disperse a scent or other chemical into the air around the In still other embodiments, the body may include a wicking material or dispersion device on an interior thereof such that the scent may be reactivated on the wicking material by pressing the body back into the original position and then expanding the accordion body again. In some embodiments, contraction and expansion of the body may dip the wicking material in a product reservoir within an interior of the body and then remove the wicking material such that the wicking material then carries a product that evaporates and disperses a scent through the body. In this manner, a user may activate the dispenser as needed to add scent to area around the dispenser.

According to other embodiments of the invention, a dispenser may include accordion sections that may be selectively opened or expanded to release a desired amount of fragrance at one time or over a period of time.

In still other embodiments, a dispenser may include one or more wicking components made from a recyclable or compostable paperboard material. In some embodiments, the paperboard material may include a plastic coating or surface to direct or control wicking. In still other embodiments, the wicking components may be shaped to provide decorative features to a dispenser.

In still other embodiments of the invention, a dispenser may be powered and may include one or more refills such that the fragrance may be dispersed over time and a refill used to change the fragrance or refill an empty dispenser.

BRIEF DESCRIPTION OF THE DRAWINGS

While the specification concludes with claims particularly pointing out and distinctly claiming particular embodiments of the present invention, various embodiments of the invention can be more readily understood and appreciated by one of ordinary skill in the art from the following descriptions of various embodiments of the invention when read in conjunction with the accompanying drawings in which:

DETAILED DESCRIPTION OF THE INVENTION

According to various embodiments of the invention, a dispenser may be used to dispense or disperse a scent, fragrance, or chemical into the air or atmosphere surrounding the dispenser. While various embodiments of the invention are described with respect to the dispensing or dispersing of a fragrance, it is understood that such embodiments of the invention could also be used to dispense or disperse a scent or chemical as well.

Figure 1:
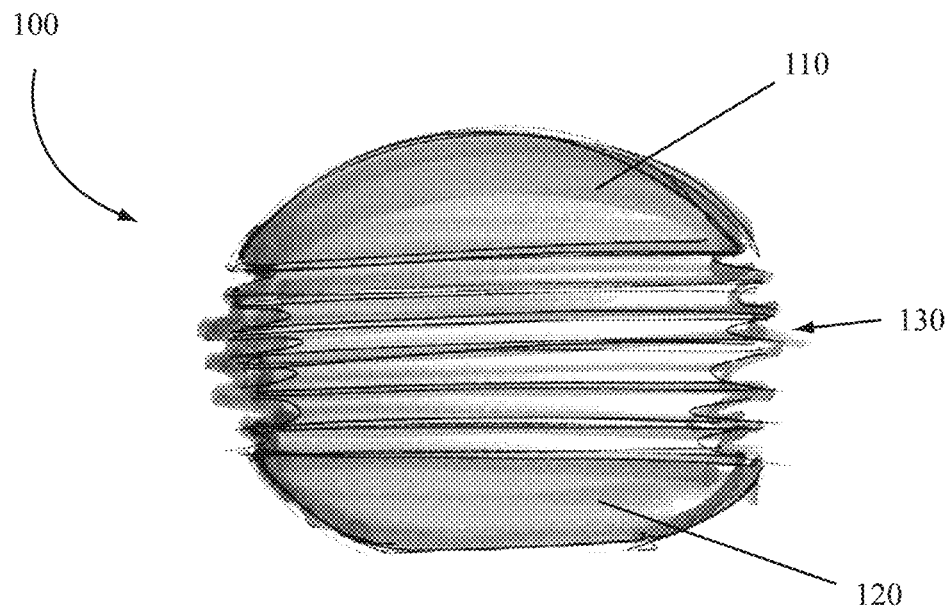
FIG. 1 illustrates a dispenser according to various embodiments of the invention.
Figure 2:
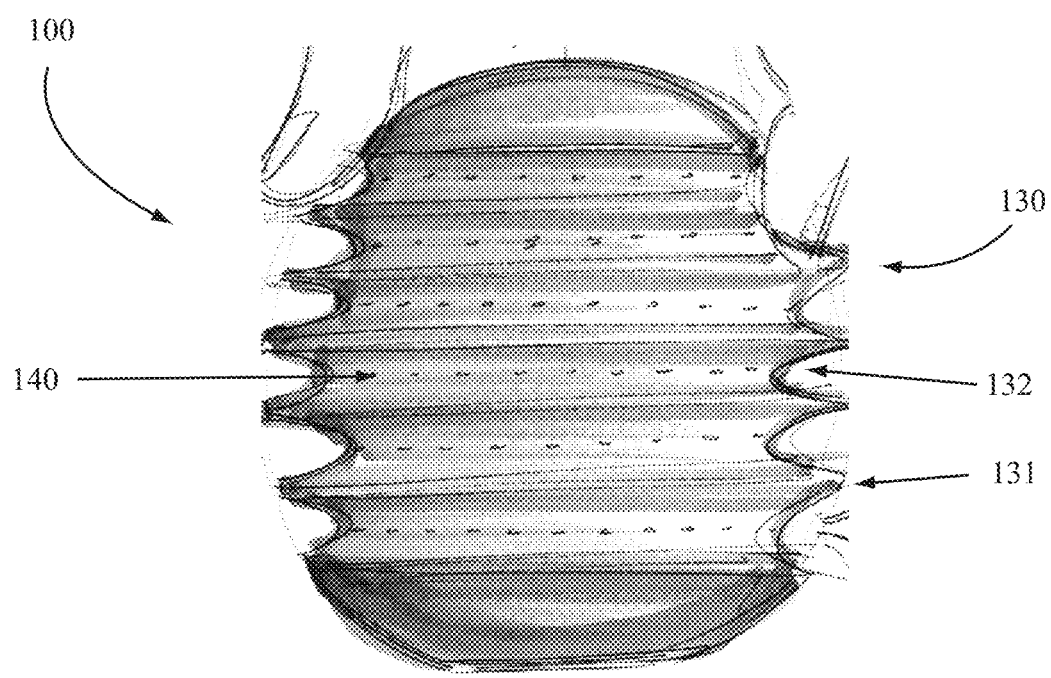
FIG. 2 illustrates a dispenser according to various embodiments of the invention.
Figure 3:
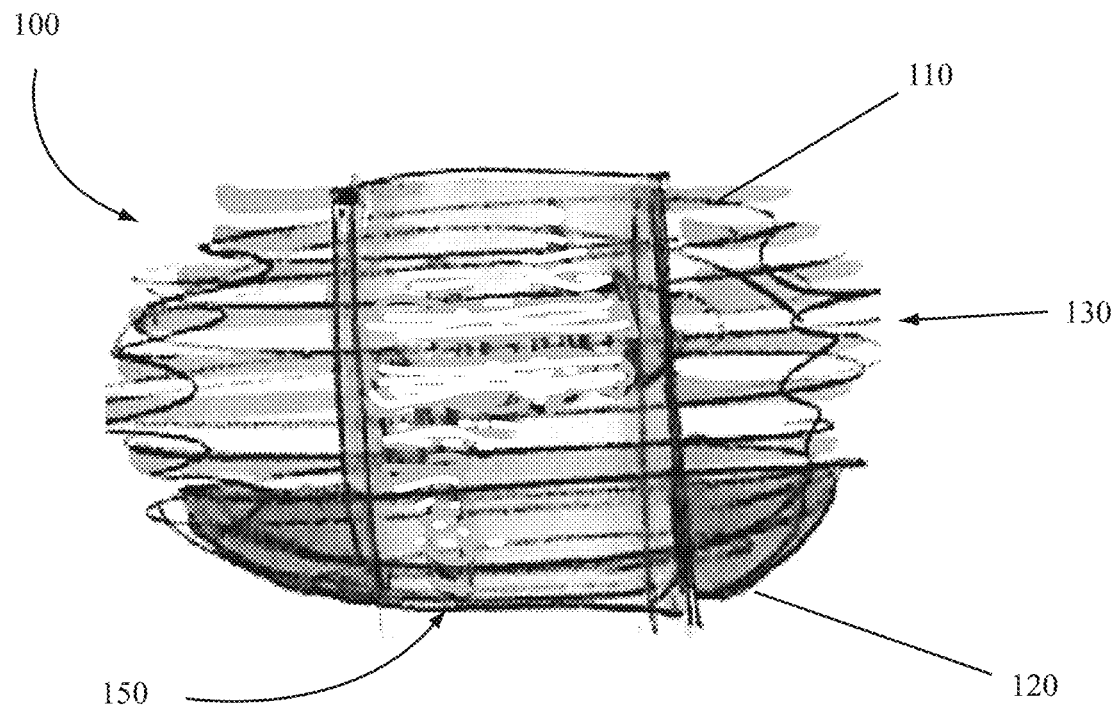
FIG. 3 illustrates a dispenser according to various embodiments of the invention.

A dispenser 100 according to some embodiments of the invention is illustrated in FIGS. 1 through 3. The dispenser 100 illustrated in FIG. 1 is in an initial—or unopened—state. The dispenser 100 may include a base 120 and a top 110. A wall 130 may extend from the top 110 to the base 120 as illustrated. In some embodiments of the invention, the wall 130 may fold-up upon itself and expand away from itself in order to allow the height or length of the dispenser 100 to be altered. For example, as illustrated in FIG. 1, the dispenser 100 includes a wall 130 that is folded over upon itself multiple times. Pulling on the top 110 of the dispenser 100 while holding the base 120 may expand the wall 130. For instance, as illustrated in FIG. 2, the wall 130 of the dispenser 100 may be expanded like an accordion. The dispenser 100 may then rest on the base 120. In other embodiments, the dispenser 100 may be inverted and the dispenser 100 may rest on the top 110 of the dispenser 100.

A dispenser 100 as illustrated in FIGS. 1 through 3 may include a hollow interior compartment. Within the interior or interior compartment of the dispenser 100, a reservoir for containing a product may exist. The reservoir may contain a liquid, gel, or other product having a fragrance or scent. Upon actuation or expansion of the wall 130 of the dispenser 100, the product may be released or unsealed within the interior dispenser 100 such that it is exposed to the environment within the dispenser 100. For instance, a flexible, plastic reservoir holding a fragrance gel or liquid product may be contained within the dispenser 100. The reservoir may include an sealed lid or cap that is connected to an interior portion of the top 110 of the dispenser 100. Upon movement of the top 110 of the dispenser 100 away from the base 120 of the dispenser 100, the top 110 may pull or remove the sealed lid or cap, exposing the product to the atmosphere within the interior of the dispenser 100.

As illustrated in FIG. 2, the wall 130 may include one or more holes 140 or passageways through the wall 130. In some embodiments, a passageway through the wall 130 may include a wicking material capable of wicking a fluid or product from an interior of the dispenser 100 to an exterior thereof. When the top 110 of the dispenser 100 is pulled away from the base 120 of the dispenser 100, the wall 130 may accordion and expand as illustrated in FIG. 2. Expansion of the wall 130 may expose the one or more holes 140 or passageways to the atmosphere surrounding the dispenser 100. At the same time, expansion may open a reservoir contained on the interior of the dispenser 100, allowing a product within the dispenser 100 to be exposed to the atmosphere. For example, air flowing through the one or more holes 140 illustrated in FIG. 2 may pass over a product within the dispenser 100 and flow back out through the one or more holes 140 with a scent or fragrance. In this manner, the fragrance may be dispersed into the atmosphere surrounding the dispenser 100.

As illustrated in FIG. 2, the dispenser 100 wall 130 may include one or more rings 131 and one or more troughs 132. The rings 131 may extend outward from troughs 132 and define an outermost edge of the wall 130. In some embodiments of the invention, the rings 131 may include a stiffened portion or a rigid structure to facilitate the integrity of the package. In still other embodiments, the rings 131 may provide protection against accidental breakage or opening of a reservoir or container on the interior of the dispenser 100 when the dispenser 100 is in an unopened or collapsed position as illustrated in FIGS. 1 and 3.

The dispenser 100 embodiments illustrated in FIGS. 1 through 3 may be made of plastic. In other embodiments of the invention, the dispenser 100 may be made of paperboard or a molded fiber material. In still other embodiments, portions of the dispenser 100 may be made of plastic and other portions may be made of paperboard. For example, the top 110 and base 120 of the dispenser 100 may be made of plastic and the wall 130 made of paperboard. In further embodiments, the material used to make the dispenser 100 may be a recyclable or compostable material such that when the dispenser 100 is used-up, it may be disposed of in a sustainable way.

While the dispenser 100 illustrated in FIGS. 1 through 3 may have a product contained on an interior thereof for dispersion into the atmosphere, in other embodiments the wall 130 of the dispenser 100 itself may contain the product to be dispersed. For instance, the wall 130 of the dispenser 100 may be made of a paperboard or other fibrous material having a scented or fragrance product embedded in the wall 130 material. In the initial—or unopened—position illustrated in FIG. 1, the wall 130 may be protected from exposure to the air or atmosphere. Upon opening the dispenser 100 to the position illustrated in FIG. 2, the wall 130 and any product embedded therein may be exposed to the atmosphere such that a fragrance or product may be dispersed into the atmosphere.

In other embodiments of the invention, the wall 130 may itself act as a wick for a product on the interior of the dispenser 100. When the top 110 of the dispenser 100 is raised or separated from the base 120, the wall 130 expands and a reservoir full of product within an interior of the dispenser 100 may be opened. The wall 130 may contact the product after the reservoir is opened and wick the product up the wall 130 where it is exposed to the atmosphere and may evaporate to release or disperse a fragrance or scent.

In some embodiments, the accordion-like wall 130 may also allow the top 110 of the dispenser 100 to be depressed after opening to collapse the wall 130 and re-wet the wall 130 with a product from an interior portion of the dispenser 100. Thus, a user may push the top 110 of the dispenser 100 down multiple times to re-wet the wall 130 and increase the amount of product on the wall 130 to be dispersed.

FIG. 3 illustrates a dispenser 100 with a wrap 150. The wrap 150 may be placed on or around the dispenser 100 to keep the dispenser 100 in an unopened state until the user is ready to use it, at which time the wrap 150 may be removed. The wrap 150 may also be used for branding, labeling, or otherwise communicating to a user how the dispenser 100 is to be used.

Figure 4:
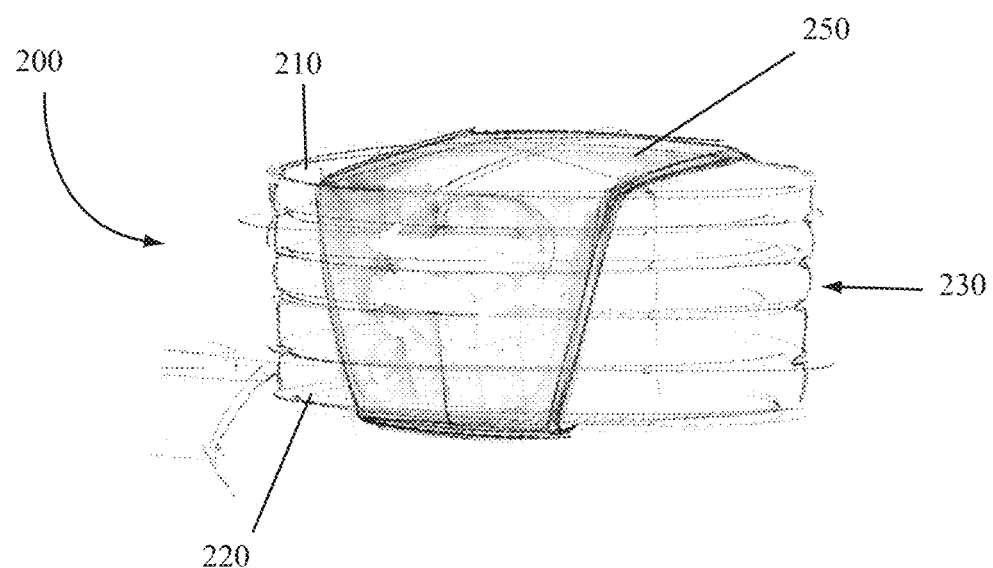
FIG. 4 illustrates a dispenser according to various embodiments of the invention.

A dispenser 200 according to other embodiments of the invention is illustrated in FIGS. 4 through 8. As illustrated in FIG. 4, the dispenser 200 may include a base 220, a top 210, a wall 230, and a wrap 250. The wrap 250 may be used in the same manner as the wrap 150 illustrated in FIG. 3.

Figure 5:
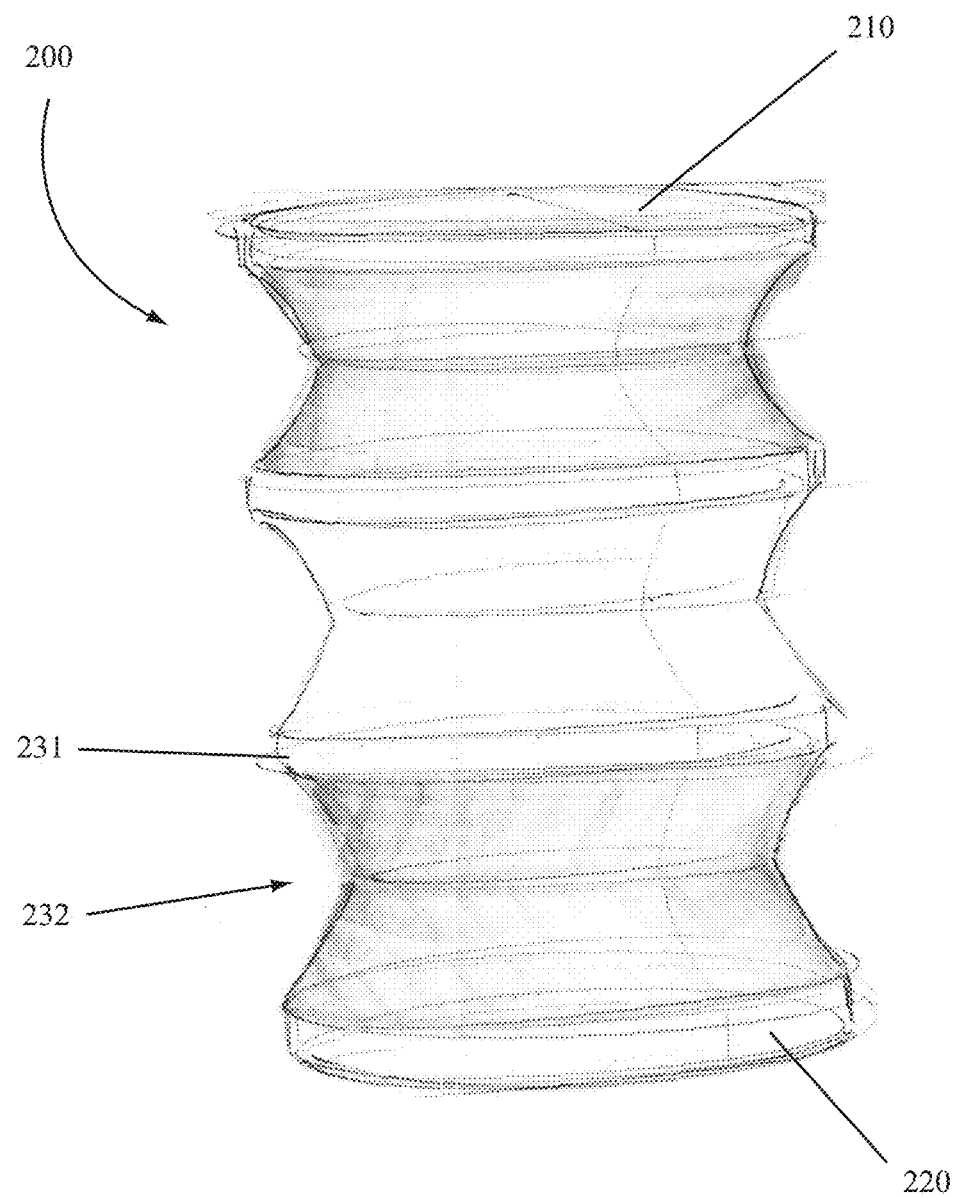
FIG. 5 illustrates a dispenser according to various embodiments of the invention.

The dispenser 200 may include rings 231 having a greater width as illustrated. The greater width of the rings 231 and larger area of the troughs 232 may be sectioned off such that the dispenser 100 may be expanded all at once or over time. For example, as illustrated in FIG. 5, a dispenser 200 may be fully expanded to open troughs 232 for dispersion of a product from the dispenser 200. According to various embodiments of the invention, as the dispenser 200 is opened, a reservoir within an interior of the dispenser 200 may be opened and product dispersed over the trough 232 material for dispersion therefrom. In other embodiments, the trough 232 material may wick product to an outer surface of the wall 230 for dispersion or may act as a material to disperse the product from an interior of the dispenser 200 to an exterior thereof.

In still other embodiments of the invention, the wall 230 material of the dispenser 200 may be imbedded with a product such that when the dispenser 200 is expanded into the position illustrated in FIG. 5, the product is dispersed over a period of time.

Figure 6:
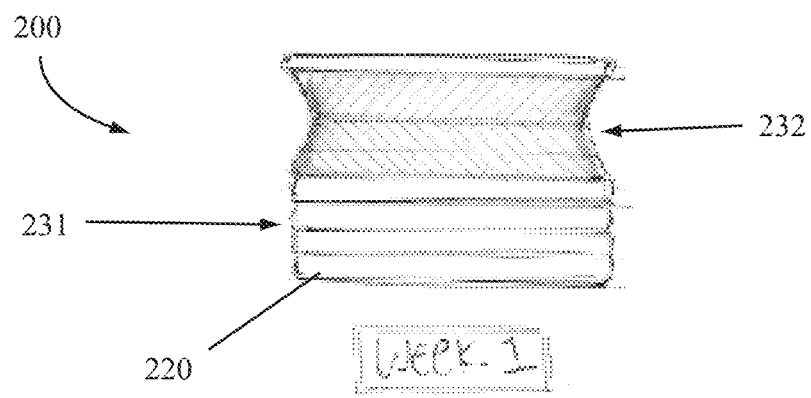
FIG. 6 illustrates a dispenser according to various embodiments of the invention.
Figure 7:
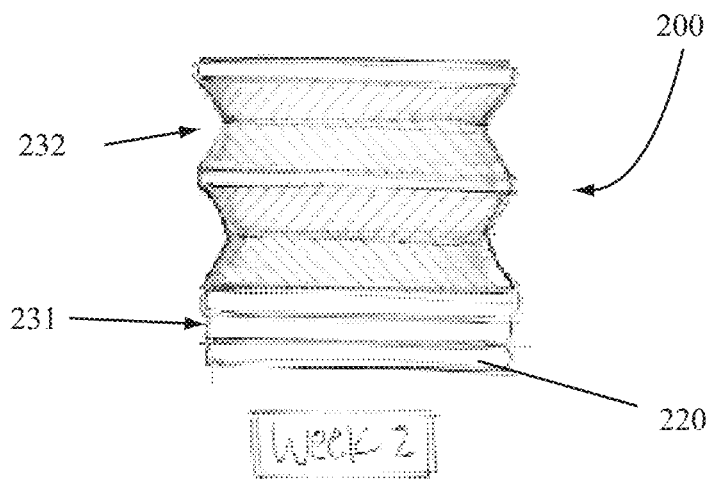
FIG. 7 illustrates a dispenser according to various embodiments of the invention.
Figure 8:
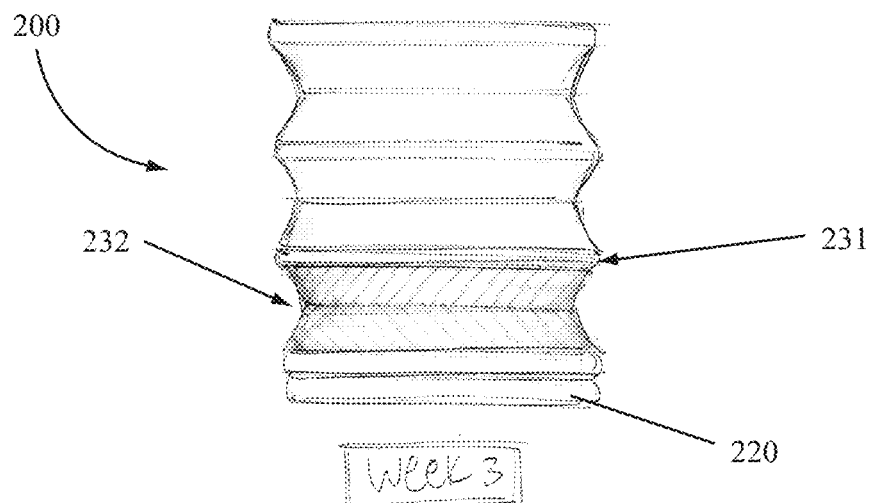
FIG. 8 illustrates a dispenser according to various embodiments of the invention.

FIGS. 6 through 8 illustrate a method of using a dispenser 200 according to certain embodiments of the invention. As illustrated, the dispenser 200 may be opened in sections such that the top 210 is separated from a first ring 231 to expose a first trough 232 as illustrated in FIG. 6. Upon such exposure, a product embedded in the wall 230 material along the trough 232 may be dispersed or a product contained on an interior of the dispenser 200 may be dispersed through holes in the trough 232, through wicking material, or through the trough 232 material itself.

A second trough 232 may be exposed by again raising the top 210 away from the base 220 as illustrated in FIG. 7. The second trough 232 area is then exposed to allow dispersion of a product contained in the wall 230 material or in the interior of the dispenser 200.

A third trough 232 may be exposed by yet again raising the top 210 away from the base 220 as illustrated in FIG. 8. The third trough 232 area is then exposed to allow dispersion of a product contained in the wall 230 material or in the interior of the dispenser 200.

While only three sections or troughs 232 of a dispenser 200 are illustrated, it is understood that the dispenser 200 may have any number of troughs 232 and rings 231. For example, a single trough 232 device without rings 231 could have just a top 210, a base 220, and a wall 230. In other embodiments, any number of troughs 232 and rings 231 could be used to form the wall 230.

As illustrated, the dispenser 200 may include multiple trough 232 portions in the wall 230 to allow a dispenser 200 to be used over longer periods of time, where a user expands a new trough 232 on a regular basis to disperse a product therefrom. In some embodiments of the invention, the first trough may be exposed to a product in the unopened state. When expanded, the first trough 232 moves to allow dispersion and the product may be put into contact with the second trough 232. When the second trough 232 is expanded, the third trough 232 may be put into contact with the product such that as new trough 232 and wall 230 portions are exposed, there is sufficient product in the exposed portion to continue to disperse a fragrance or scent.

In other embodiments of the invention, a dispenser 200 may be used to disperse a little to a lot of a fragrance at one time. If just a faint fragrance or scent is desired, a single trough 232 may be exposed. If a greater amount of fragrance or scent is desired, multiple troughs 232 may be exposed at once.

Figure 9:
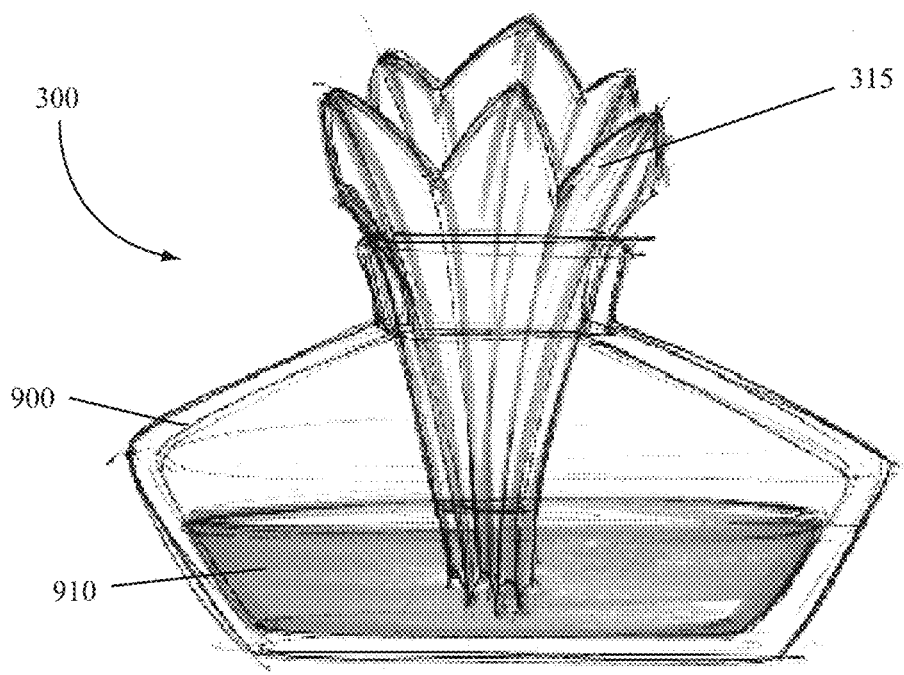
FIG. 9 illustrates a dispenser according to various embodiments of the invention.
Figure 10:
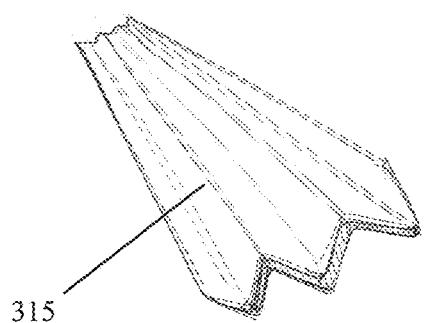
FIG. 10 illustrates a dispenser according to various embodiments of the invention.
Figure 11:
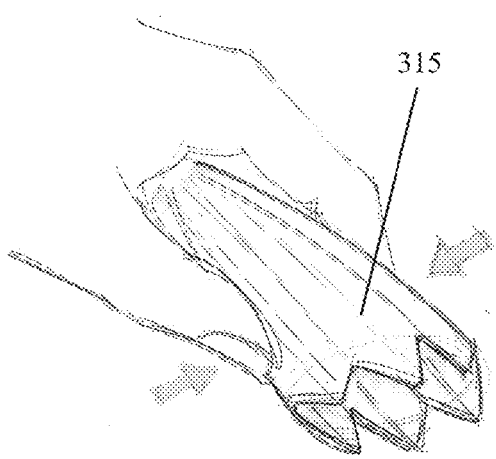
FIG. 11 illustrates a dispenser according to various embodiments of the invention.

A dispenser 300 according to still other embodiments of the invention is illustrated in FIGS. 9 through 11. As illustrated, a dispenser 300 may include a container 900 holding a product 910. A wick 315 made of a paperboard or plastic material may be inserted into the container 900 to contact the product 910 and wick the product into the wick 315. Evaporation of the product 910 form the wick 315 may disperse a fragrance or scent into the atmosphere.

As illustrated in FIGS. 10 and 11, the wick 315 may come folded in a compact form or shape. User expansion of the wick 315 may open the wick 315 to provide a larger surface area for evaporation of a product 910 in the wick 315. The wick 315 may then be inserted into the container 900 and into the product 910.

According to various embodiments of the invention, a kit for dispersing a fragrance or scent may be produced and sold. The kit may include a container 900, one or more vials or packages of a product 910 and one or more wicks 315. The user may open the kit, add product 910 to the container 900 and insert the desired wick 315 to create a customized dispenser 300. The kit may include products 910 having different fragrances. The kit may also include different shaped wicks 315 and different sized wicks 315. For instance, the wicks 315 may be made of a paperboard material or a paperboard and plastic material to control the rate of evaporation off of the wick 315. In addition, the wicks 315 may include different designs so that a user could pick a wick 315 in the shape of a column or of their favorite flower. The wicks 315 may also be recyclable or compostable, as may be the container 900.

Figure 12:
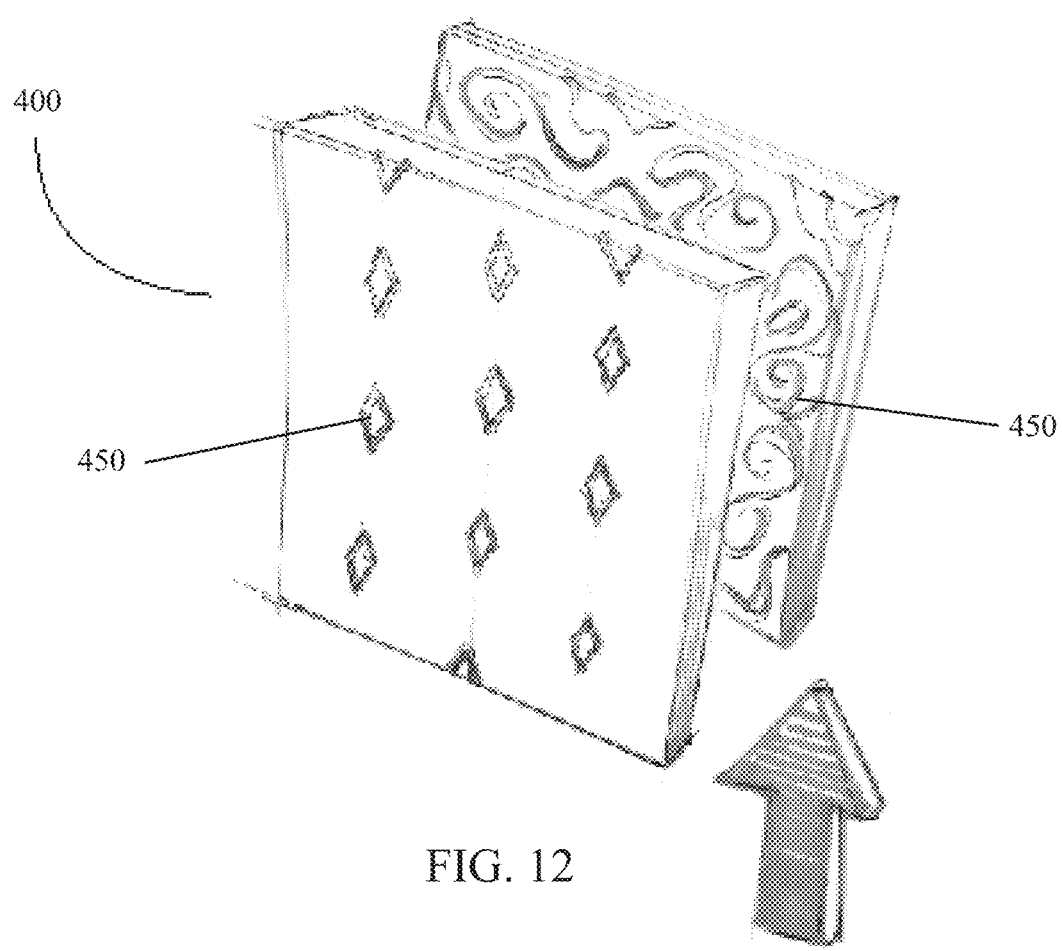
FIG. 12 illustrates a dispenser according to various embodiments of the invention.

A dispenser 400 according to still other embodiments of the invention is illustrated in FIG. 12. As illustrated, the dispenser 400 may include a wall or walls having wicking features 450 through which a product may be exposed to the atmosphere to disperse a scent or fragrance. The dispenser 400 may be made of a paperboard material or a paperboard and plastic mixed material. The dispenser 400 may be placed in a pool of product. Upon contacting a product, the wicking features 450 may draw the product up the dispenser 400 and allow evaporation of the product or dispersion of a fragrance or scent.

In other embodiments, a product may be contained within the dispenser 400 such that when the dispenser 400 is cracked or the integrity of the dispenser 400 is altered, a product is released within the dispenser 400. Once released, the product may follow the wicking features 450 within the dispenser 400, wetting those features and allowing dispersion of a fragrance or scent. For example, a vial or pouch of product may be stored on an interior of the dispenser 400. When the vial or pouch is cracked or opened by the user, the product is released, contacting the wicking features 450 and wetting those features. Air passing over an exterior portion of the dispenser 400 may evaporate product, releasing a scent or fragrance into the air.

Figures 13, 14:
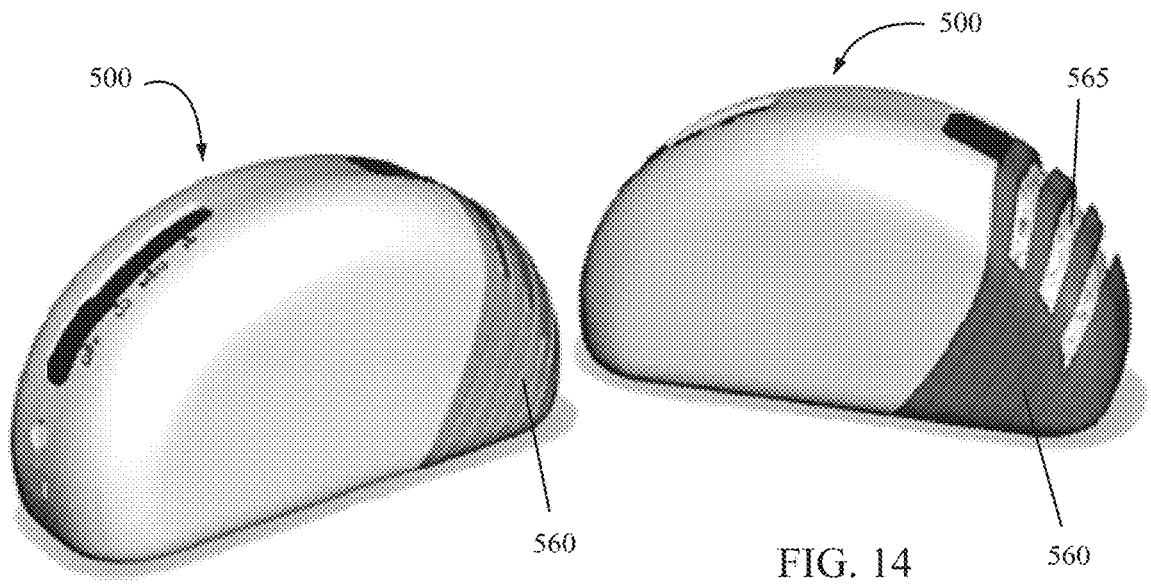
FIG. 13 illustrates a dispenser according to various embodiments of the invention.
FIG. 14 illustrates a dispenser according to various embodiments of the invention.
Figure 15:
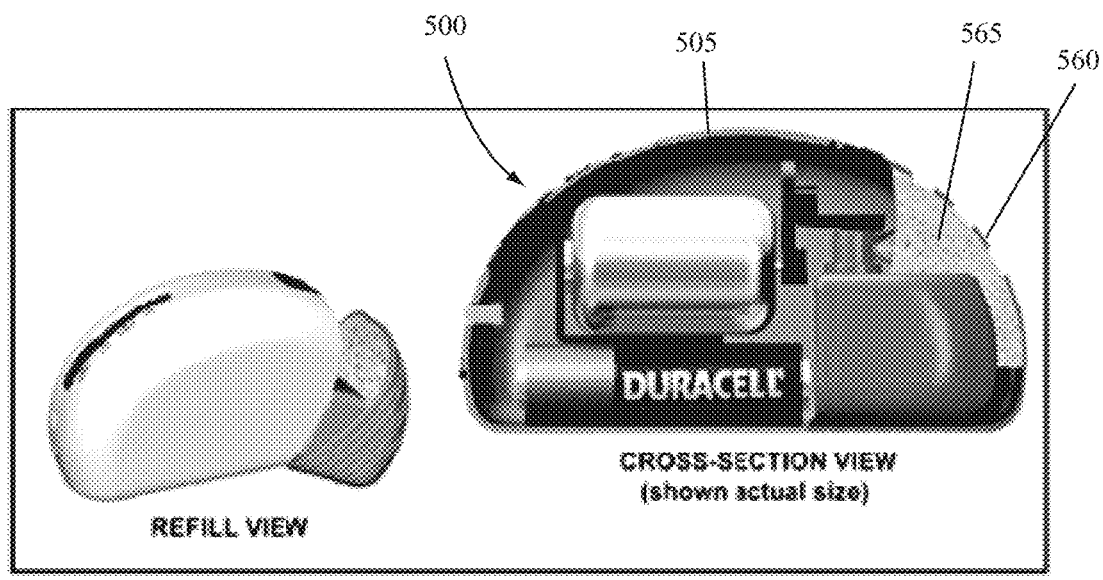
FIG. 15 illustrates a dispenser according to various embodiments of the invention.

A dispenser 500 according to still other embodiments of the invention is illustrated in FIGS. 13 through 15. As illustrated, the dispenser 500 may include a shell 505 within which is contained a motor and power-source (such as a battery). The motor may drive a fan or heat source directed at a gel fragrance insert 565. The gel fragrance insert 565 may be contained in a refill cartridge 560 attached to the shell 505 of the dispenser 500 as illustrated in FIG. 15.

In operation, a user may select a level of desired fragrance and set the dispenser 500 accordingly. Once set, the dispenser 500 may actuate the motor to apply heat or a flow of air over the gel fragrance insert 565, causing the dispersion of a fragrance or scent at the desired, set level. When the gel fragrance insert 565 has expired or no longer produces a scent, the refill cartridge 560 may be replace with a new scent or fragrance as desired.

While various embodiments of the invention include a gel fragrance insert 565, it is understood that a porous material may be used with a liquid product added to the material instead. In still other embodiments, an insert having a fragrance embedded in the insert for slow release may be used instead of the gel fragrance insert 565.

What is claimed is:

1. A dispenser, comprising:
   a top;
   a base;
   a wall between the top and the base extending along an axial length of the dispenser, the wall including a plurality of rings and a plurality of troughs, wherein the wall is folded onto itself in an unopened configuration and is expanded in an opened configuration; and
   a product in the dispenser,
   wherein the wall includes at least two additional configurations, a first configuration wherein one of the plurality of troughs is unfolded from itself and the remainder of the plurality of troughs are folded onto themselves, and a second configuration wherein at least two of the plurality, but not all of the plurality, of troughs are unfolded from themselves and the remainder of the plurality of troughs are folded onto themselves,
   wherein the plurality of troughs are parallel to one another in at least the open, unopened, first and second configurations,
   wherein the plurality of rings and troughs form a self-supporting accordion structure that selectively maintains the axial length of the dispenser when said wall is in one of said first and second configurations,
   wherein the wall comprises a porous absorbent material and is configured to wick the product from an interior of the dispenser to an exterior of the dispenser, and
   wherein the porous absorbent material is shielded from exposure to air in at least the unopened configuration.

2. The dispenser of claim 1, wherein the product is contained within the interior of the dispenser.

3. The dispenser of claim 1, wherein the product is embedded in the wall of the dispenser.

4. The dispenser of claim 2, further comprising a reservoir on the interior of the dispenser, wherein the reservoir holds the product and the product is a volatile scent or fragrance.

5. The dispenser of claim 3, wherein the wall comprises a paperboard material.

6. The dispenser of claim 3, wherein the base, the top, and the wall each comprise a paperboard material.

7. The dispenser of claim 4, further comprising a plurality of holes in the wall.

* * * * *